United States Patent [19]

Clay

[11] Patent Number: 4,541,292

[45] Date of Patent: Sep. 17, 1985

[54] SAMPLING DEVICE

[75] Inventor: William Clay, Sheffield, England

[73] Assignee: Land Pyrometers Limited, Sheffield, England

[21] Appl. No.: 507,121

[22] Filed: Jun. 22, 1983

[30] Foreign Application Priority Data

Jul. 7, 1982 [GB] United Kingdom ............. 8219719
Feb. 9, 1983 [GB] United Kingdom ............. 8303557

[51] Int. Cl.$^4$ ............................................. G01N 1/12
[52] U.S. Cl. .................................... 73/864.55; 29/428; 73/864.57; 73/864.59
[58] Field of Search ............ 73/864.53, 864.54, 864.55, 73/864.56, 864.57, 864.58, 864.59; 29/428; 264/219, 225, 226; 164/6, 15, 37, 44

[56] References Cited

U.S. PATENT DOCUMENTS

| 3,455,164 | 7/1969 | Boyle | 73/864.55 |
| 3,994,172 | 11/1976 | Kelsey | 73/864.55 |
| 4,116,070 | 9/1978 | Falk . | |
| 4,140,019 | 2/1979 | Falk . | |
| 4,237,734 | 12/1980 | McDevitt | 73/425.4 R |
| 4,296,638 | 10/1981 | Kolb | 73/864.57 |
| 4,325,263 | 4/1982 | Gaines, Jr. et al. | 73/864.55 |
| 4,361,053 | 11/1982 | Jones et al. | 73/864.53 |

FOREIGN PATENT DOCUMENTS 1508974 3/1974 United Kingdom .
1572122 3/1977 United Kingdom .
1602702 4/1978 United Kingdom .

Primary Examiner—S. Clement Swisher
Attorney, Agent, or Firm—Jeffers, Irish & Hoffman

[57] ABSTRACT

A metal melt sampling device comprises a support tube; and a sampling unit of refractory material mounted in the support tube. The sampling unit includes first and second portions the second portion being integral with the first portion and defining with a pair of metal plates the walls of a main sample cavity. At least one of the first and second portions is a push fit in the support tube. An inlet passage is provided to enable metal melt to pass in use from a leading end of a unit to the main sample cavity.

18 Claims, 8 Drawing Figures

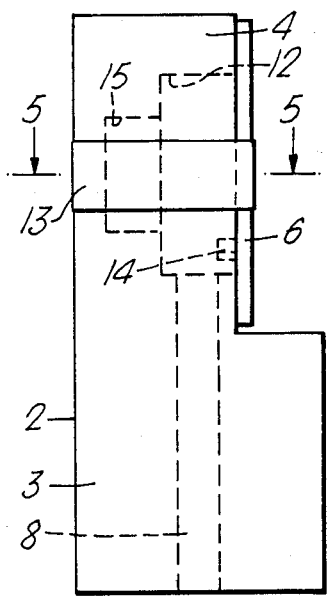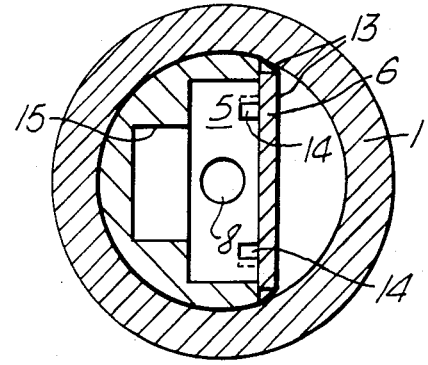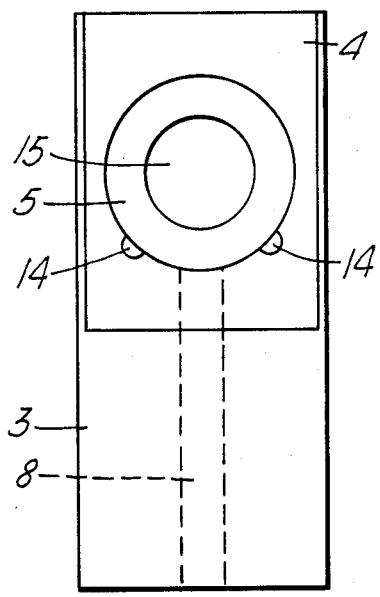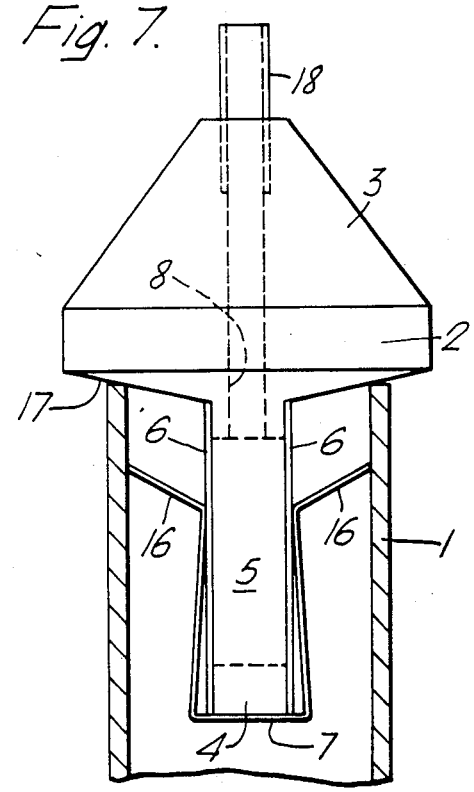

SAMPLING DEVICE

The invention relates to a metal melt sampling device.

In the iron and steel industries it is necessary to carry out tests on samples of iron and steel so that the quality of the metal melt can be closely controlled. Up to now, the sampling of iron and steel melts has been treated separately and different sampling devices have been developed for sampling each type of melt, the devices also differing depending upon the conditions under which the melt is sampled. In general, metal melt sampling can be divided into a number of areas depending upon whether the melt is of iron or steel and whether sampling is carried out from a bath of the metal melt or a moving stream of the metal melt. Different technologies have been developed for each type of sampling due to the differences in viscosity and melting point of iron and steel and the different sampling environments: bath or stream sampling.

A typical sampling device which has been used for many years comprises a pair of metal mould halves defining a substantially circular sample cavity and an inlet passage communicating with the cavity, the metal mould halves being held together by a clip and the inlet passage extending into a rubber, cork or ceramic bung which is pushed into a paperboard tube and from which a silica tube extends. This type of sampling device is commonly called a "lollipop" device. The purpose of the silica tube is to provide a non-shattering, non-stick, non contaminating vehicle to transmit melt to the sample cavity and to provide a secondary sample.

When the lollipop device is used in sampling iron, the metal moulds are normally made of copper which is an extremely good conductor of heat and enables iron in the sample cavity rapidly to cool and form a rigid sample. If more inefficient heat conducting metals are used for the mould then there is a danger that due to its relatively low melting point, unsolidified iron will flow out of the inlet passage as the unit is withdrawn from the bath resulting in a poor sample. It is also important with iron sampling to obtain a pin sample for analysis.

With steel sampling it is often necessary to deoxidise or kill the steel sample and this requires the provision of a mixing chamber if a homogeneous pin sample is required.

The construction of all these earlier sampling devices is complex. Each requires a two part mould, some means of supporting the mould within a paperboard tube, normally a rubber, cork or ceramic bung, one or more silica tubes (particularly where a pin sample is obtained), and where necessary a mixing chamber. These are expensive to provide and assemble and it is desirable to simplify these constructions.

One attempt at simplification is shown in European Specification No. 2716 which discloses a two part mould of rectangular shape with metal plates provided on the outer surfaces to define a sample cavity. The mould is supported in a paper board tube of circular cross-section and is sealed therein by means of bonded sand. Furthermore, a silica entry tube is also necessary. This construction does not solve the problems outlined above since although it has a reasonably compact form, it is not readily mounted within the paper board tube and still requires the same or more component parts than the earlier constructions.

Another sampling device is illustrated in European Patent Specification No. 18514, in this case in association with a thermocouple. Again, the sampling device comprises a two part mould mounted within a paper board tube and as with the construction just described, does not result in a reduction in the number of parts required for its manufacture.

One further proposal which has been made recently is shown in British Patent Specification No. 1,508,301. In some of the examples shown in this specification, the sampling device is formed by a one piece body of a mineral fibre insulating material forming a sample cavity which is closed by metal plates on a clamp. In one construction, the device is slotted into a paper board outer tube, into which the clamp extends, with silica tubes extending through the end of the paper board tube, against which the device rests, into the metal melt. Again, this is complex in construction, any possible simplification being nullified by the use of a complex clamping arrangement.

In accordance with the present invention, a metal melt sampling device comprises a sampling unit of refractory material for mounting in a support tube, the sampling unit including first and second portions, the second portion being integral with the first portion and defining with further means the walls of a main sample cavity, at least one of the first and second portions being a push fit in the support tube, and an inlet passage being provided to enable metal melt to pass in use from a leading end of the unit to the main sample cavity.

With this completely new construction, a very much simplified sampling device is achieved. The previous use of two mould halves and a separate bung has been replaced by an integral unit which can be simply push fitted into the support tube.

Preferably, the further means comprises one or more metal plates which are connected to the second portion of the unit to close the main sample cavity. This is particularly convenient since depending upon the type of sample being extracted (steel or iron) the thickness and type of metal plate can be selected appropriately. Preferably, the second portion of the sampling unit has a pair of opposed openings over which a pair of metal plates are secured.

The or each plate may be secured to the second portion of the sampling unit by a clip having at least one outwardly extending portion whereby on insertion of the sampling unit into the support tube, the or each outwardly extending portion of the clip is forced radially inwardly to assist in securement of the or each plate on the second portion of the sampling unit.

This type of securement has been found to be particularly effective and holds the plates firmly on the sampling unit. Preferably, the clip is generally U-shaped, portions of the clip adjacent the bight of the U converging and the arms of the clip subsequently diverging to an extent sufficient that, in use, when the clip is mounted on the second portion of the sampling unit, the diverging portions of the clip engage the support tube. Where a single plate is provided, a suitable groove should be provided in the second portion of the sampling unit to receive the arm of the clip not abutting the plate.

Preferably, a secondary pin sample tube is provided in the first portion of the sampling unit in communication with the main sample cavity. Conveniently the secondary pin sample tube is formed by a blind bore. This is particularly convenient since it simplifies the production of the unit. Thus, two bores may be moulded into the unit when it is formed and the secondary pin sample tube can be formed simply by blocking off one of the bores at the leading end of the unit, the other bore forming the inlet passage.

Alternatively or additionally a secondary pin sample tube could be provided in the second portion.

It is often necessary when sampling a metal melt to obtain a sample whose weight and dimensions are accurately known. A pin sample is not necessarily the best way of achieving this since the size of the pin which is essentially the same as that of the entry passage for ease of construction, is often too large and the pin sample must be prepared and broken up to provide a specific weight for analysis. Furthermore, during manufacture, an additional step is required to block one of the bores initially provided in the device in order to obtain the pin sample tube. Preferably therefore the device further comprises at least one additional sample cavity defined by the second portion of the sampling unit and the further means, the or each additional sample cavity communicating with the main sample cavity.

By defining additional sample cavities with the second portion and the further means, preferably a metal plate, a more simplified construction is obtained. Thus, a simple depression, groove or other indentation may be made in the second portion and this is then covered by a metal plate.

Preferably, the or each additional sample cavity is considerably smaller than the main sample cavity. It has been found that such a small additional sample cavity is very well suited to the production of metal samples of known weight and shape. The additional sample cavity can be of any desired shape and one convenient shape is semi-cylindrical. This is convenient because the formation of such an additional sample cavity in the sampling unit is fairly simple to achieve using a circularly cylindrical mould piece which partly overlaps the main sample cavity. Alternatively, the or each additional sample cavity may be wedge shaped. This shape is particularly advantageous since it can be easily cleaned and polished using a grinding wheel.

The position of the additional sample cavities relative to the main sample cavity can also be selected as required but in some cases it is believed to be advantageous to provide the additional sample cavities adjacent the inlet passage. The reasons for this include the fact that the additional sample cavities are then filled under gravity, and that after the metal sample has solidified it is commonly transported with conveying air through tubes and the metal which has solidified in the inlet passage tends to protect these relatively small additional samples.

For the purposes of analysis, it is necessary for a sample of metal melt to be thin and to have at least one flat circular surface. This is achieved by suitably shaping the main sample chamber but the flat surface or surfaces obtained are not usually of a high enough quality to enable analysis to be carried out. The surface thus has to be machined by milling or grinding.

In the past, various methods have been proposed for preparing a surface of the sample for analysis. The most common is to grip the narrow edges of the sample and then to press the sample down on a spinning grinding disc. Clearly, since only a narrow edge is gripped, the sample is not securely held and there is a significant risk of failure.

A second method is to place the sample in a profiled vice with the face of the sample to be machined upwards. This face is then ground or milled in the usual way. This method enables the sample to be gripped more securely but has the disadvantage of requiring the provision of profiled vice.

A further method which has recently been proposed comprises dropping the sample down a slot of varying width so that samples of different sizes can be accommodated. Grinding or milling wheels are then brought into contact with opposite faces of the sample to provide two surfaces suitable for analysis. Again, a complex apparatus is required to provide the surface.

Preferably, a portion of the walls in the main sample cavity are shaped to produce, in use, a locating formation in the sample of metal melt, whereby a solidified sample extracted from the main sample cavity may be located by the locating formation during preparation of the surface of the sample for analysis.

With this feature, a locating formation is moulded with the metal melt sample and provides a secure means for locating a surface of a sample during grinding or milling. No complex holding apparatus is required and the shape of the locating formation may be selected to be suitable for whatever holding apparatus is to be used.

Preferably, the portion of the walls of the main sample cavity which is shaped to produce the locating formation is that portion opposite to a portion of the walls which holds the surface of the sample for analysis. This enables pressure to be exerted on the surface for analysis via the locating formation during machining.

It is particularly convenient if the portion of the walls of the main sample cavity shaped to produce the locating formation is a recess whereby after solidification, the metal sample has a protruding boss integrally formed on it to provide the locating formation.

One of the most important advantages of this device which has been discovered is that it can be used for any type of metal melt sampling and furthermore the use of conventional silica tubes can be substantially eliminated. If the material of the unit cannot withstand the metal melt on initial contact then it has been discovered that simply by coating the exposed surface of the sampling unit and a portion of the inlet with refractory cement no silica tube is required. This is because the sample of the metal melt is contaminated primarily by material of the unit adjacent the entrance to the inlet passage which is attacked by the metal melt. As the melt reaches the much larger main sample cavity, the rate of entry of melt into the cavity decreases and very little contamination occurs. It is convenient, however, to coat the entire surface of the sampling unit with refractory cement since this can simply be achieved by dipping the sampling unit into molten refractory cement. If a pin sample tube is provided then it is desirable to coat this with the refractory cement in order to obtain suitable pin samples for analysis. As will be appreciated, the avoidance of the use of silica tubes is extremely important in simplifying construction and decreasing the cost of the device.

The only occasions on which a silica inlet tube is required are firstly the cases of suction and stream sampling where it is not desirable to position the leading end of the sampling device in the stream and preferably a short silica tube is mounted in the inlet passage in order to guide metal melt from the stream into the device. In the past, it has been necessary with stream samplers to use a flexible bung in order to compensate for forces on the mould/bung connection. Of course, in the present construction, such a problem does not arise since the "bung" is integral with the mould. Secondly, in ingot sampling where the temperature at the top of the bath will be relatively low, a short silica tube may be necessary to space the melt entry point from the leading end of the unit in order to prevent chilled metal from blocking the entry passage.

Preferably, the sampling device includes the support tube which may be made of paperboard and a paperboard cover may be provided over the leading end of the support tube to protect the sampling unit on insertion into the metal melt. This is particularly advantageous and is possible because of the omission in general of the standard silica inlet tube. The advantage lies in the fact that metal slag does not adhere to the paperboard cover which quickly disintegrates and which is considerably cheaper than the conventional metal slag cap.

In one convenient arrangement, when the sampling device according to the invention is used as a stream sampler, the first portion of the sampling unit is arranged to protrude from, and abut a leading end of the support tube, the first portion tapering towards the leading end of the unit, the second portion of the sampling unit being push fitted into the support tube, and a silica inlet tube being mounted in and protruding from the inlet passage.

By tapering the first portion towards the leading end of the unit the need for a long silica inlet tube is avoided and a small stub tube is sufficient.

In the case of steel sampling where it is necessary to kill the steel, we have found that it is sufficient to provide aluminium within the inlet passage and a separate mixing chamber is not required.

The support tube itself may form or be connected, in use, to, a conventional lance.

Typically, the sampling device including the support tube will be disposable in the sense that it is used to extract one sample and is then destroyed to gain access to the sample. However, in alternative constructions, particularly in the case of stream sampling, the support tube may be metal and reusable while just the sampling unit is disposable.

It is particularly convenient if the sampling unit is made of bonded sand.

In one example, a method of manufacturing a sampling device in accordance with the invention comprises providing moulding apparatus having means for defining the main sample cavity; supplying bondable sand to the moulding apparatus and allowing the sand to solidify to define a sampling unit; extracting the solidified unit; securing one or more metal plates on the unit to close the sample cavity; providing an inlet passage; and mounting the sampling unit in a support tube.

The use of bondable sand is particularly advantageous since in view of its cheapness it enables sampling devices to be made on a large scale, and it is, furthermore, very easy to mould allowing complex shapes easily to be moulded. Preferably, the bondable sand comprises resin bondable sand or carbon dioxide sand.

In another example, a method of manufacturing a sampling device in accordance with the invention comprises providing moulding apparatus having means for defining the main sample cavity; moulding green ceramic with the moulding apparatus; heating the moulded ceramic to form a sampling unit; securing one or more metal plates on the unit to close the sample cavity; providing an inlet passage; and mounting the sampling unit in a support tube.

Although an inlet passage could be bored through the moulded unit, it is preferable if the moulding apparatus has means for defining the inlet passage.

Conveniently, the method further comprises coating at least part of the unit with refractory cement.

Apparatus for use in such a method may include moulding apparatus comprising a bottom plate having an upright rod for defining an inlet passage, two movable side plates which have means defining a sample cavity, and a top plate with an opening through which bondable sand may be supplied in use.

With this apparatus, the plates are assembled together and sand is then supplied under pressure through the top plate into a cavity defined by the plates. Preferably, the side plates are heated prior to introduction of the sand by means of a flame while the bottom plate is heated with an electrical heater. After the sand has solidified, the movable plates are moved aside and the unit in turn is removed.

The means for defining the sample cavity may comprise a pair of bosses integral with the plates.

Some examples of devices in accordance with the invention will now be described with reference to the accompanying drawings, in which:

FIG. 4 is a side elevation of a second example of a device with the support tube removed;

FIG. 5 is a section taken on the line 5—5 in FIG. 4 but with the support tube added;

FIG. 6 is a front elevation of the device shown in FIG. 4 with the metal plate removed;

FIG. 7 is a part sectional view of a third example; and,

Figure 1:
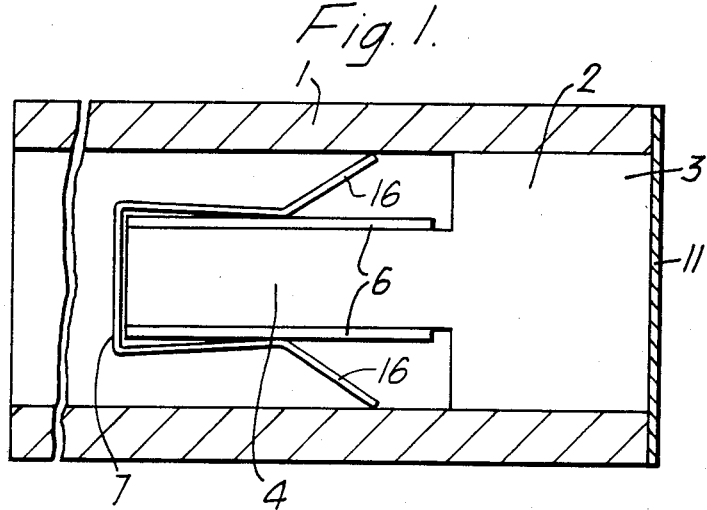
FIG. 1 is a part sectional view of one example.
Figure 2:
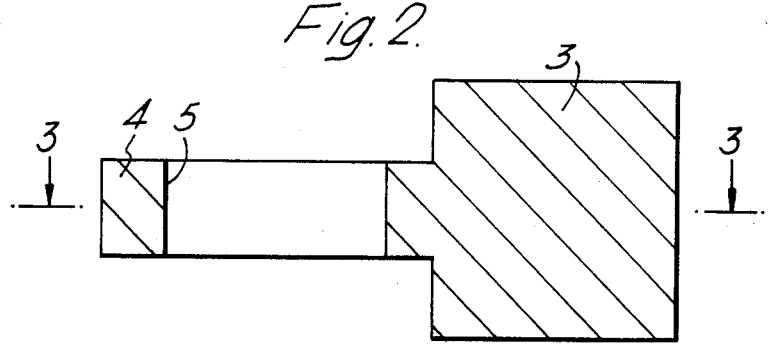
FIG. 2 is a cross-section through the sampling unit of the example shown in FIG. 1.
Figure 3:
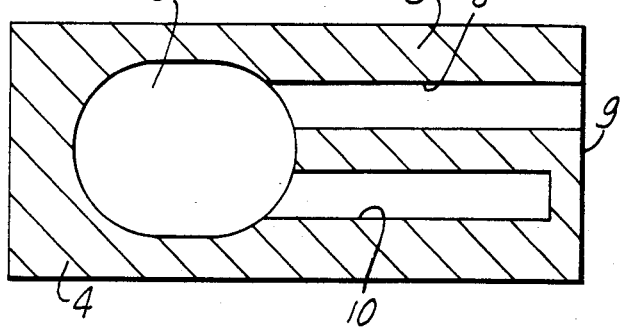
FIG. 3 is a section taken on the line 3—3 in FIG. 2.

The sampling device shown in FIGS. 1 to 3 comprises a paperboard tube 1 of circular cross-section in which is mounted a sampling unit 2 formed of bonded sand. The sampling unit 2 comprises a first portion 3 of circular cross-section push fitted into the paperboard tube 1 and an integral second portion 4 defining part of an oval shaped sample cavity 5 (FIG. 3). The sample cavity 5 is closed by a pair of metal plates 6 held on the second portion 4 by a generally U-shaped metal clip 7. The clip 7 is arranged such that when the clip is positioned on the second portion 4 its ends 16 will extend beyond the inner diameter of the paperboard tube 1 so that on insertion of the unit into the paperboard tube 1, the arms 16 will be forced radially inwardly to urge the plates 6 against the second portion 4. In this case, the sampling unit 2 is secured in the paperboard tube 1 by virtue of the second portion 4 also being a push fit in the support tube 1.

An inlet passage 8 having a circular cross-section extends from a leading end face 9 of the sampling unit 2 through the first portion 3 into the cavity 5. A secondary pin sample tube 10 extends from the cavity 5 parallel with the inlet passage 8 towards the leading end face 9 of the sampling unit 2. The secondary pin sample tube 10 is closed at the leading end face of the unit 2 to form a blind bore.

The leading end face 9 of the sampling unit 2, the secondary pin sample tube 10 and the first few millimeters of the inlet passage 8 are each coated with refractory cement to prevent damage occurring on contact with metal melt. Typically, and conveniently both the inlet passage 8 and the secondary pin sample tube 10 have the same diameter, for example 6 mm.

In use, the sampling unit 2 is push fitted into the paperboard tube 1 the other end of which (not shown) forms a socket which receives a spigot portion of a conventional lance. Normally, a thin paperboard disc 11 is glued or tacked to the paperboard tube 1 across the leading end face 9 of the sampling unit to protect the leading end face during initial insertion into metal melt. When the device is inserted into metal melt, the paperboard disc 11 will disintegrate and metal melt will pass through the inlet passage 8 into the main sample cavity 5. Melt will also pass out of the cavity 5 into the secondary pin sample tube 10. When the main sample cavity 5 has been filled, the device is removed from the metal melt and the paperboard tube 1 and the sampling unit 2 are destroyed to obtain the solidified metal sample.

The device illustrated in FIGS. 4 to 6 is different from that shown in FIGS. 1 to 3 in that the second portion 4 has a single recess 12 defining the sample cavity 5 which is covered by a single metal plate 6. The metal plate 6 is retained on the second portion 4 by paper tape 13, although a clip could be used by suitably recessing the second portion 4 of the unit 2, or the plate 6 could be sized to interfere with the support tube 1.

Additional sample cavities 14 are provided in the second portion 4 in communication with the main sample cavity 5. Typically, the main sample cavity 5 may have a diameter of 35-40 mm while each additional sample cavity 14 may have a height of about 5 mm.

A further recess 15 is moulded in the second portion 4 in communication with the recess 12 defining the main cavity 5.

In use, metal melt passes into the main sample cavity 5 as previously described and also into the additional cavities 14 and the recess 15. After solidification, the sample extracted from the device will have a substantially flat, circular surface defined by the metal plate 6, and two ears defined by the additional cavities 14. The solidified sample will also have, extending from the side opposite to the flat side, a boss which was moulded by the recess 15. The ears are then broken off to provide two samples of known shape and weight while the sample defined by the main sample cavity 5 is gripped by the boss formed in the recess 15 and the flat surface of the sample is then pressed down onto a milling or grinding wheel to machine the flat surface into a form suitable for subsequent analysis.

FIG. 7 illustrates a stream sampler. In this example, the second portion 4 of the sampling unit is substantially the same as that shown in FIG. 1. The first portion 3 of the unit 2 has a generally frustoconical form and has a trailing end face 17 resting against the leading end of the paperboard tube 1. The advantage of forming the first position 3 with a tapering shape is that although a silica tube 18 is necessary this can be comparatively short. As may be seen in FIG. 7, the silica tube 18 is glued or cemented into the inlet passage 8.

Figure 8:
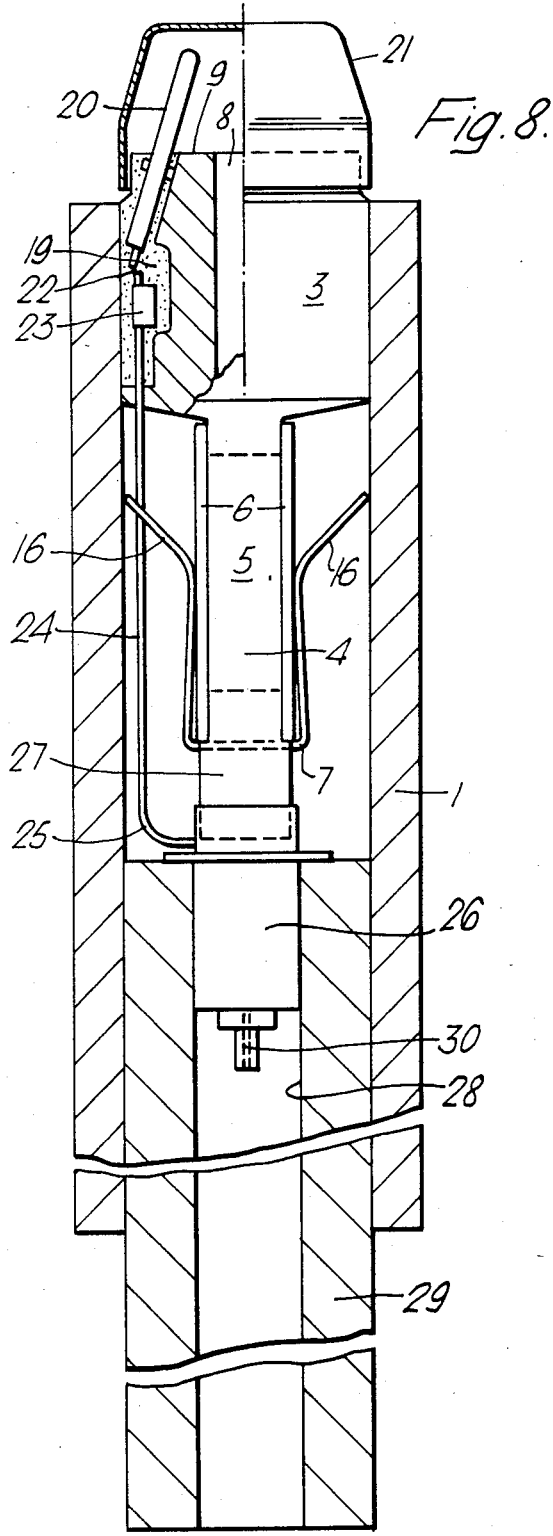
FIG. 8 is a part sectional view of a fourth example.

The example illustrated in FIG. 8 shows how a temperature sensing device, in this case a thermocouple, can be incorporated into the sampling device. The sampling device illustrated comprises a sampling unit 2 the second portion 4 of which is substantially the same as that shown in FIG. 7, the first portion 3 being similar to that shown in FIG. 1 although in this case a secondary pin sample tube 10 is not provided. The first portion 3 has a recess 19 formed in its radially outer surface opening at the leading end face 9 of the unit and a thermocouple 20 is cemented into the recess 19, A conventional slag cap 20 is push fitted over the temperature sensing device 20. The wires 22 from the thermocouple 20 are welded at 23 to stiff copper wires 24 which extend past the second portion of the sampling device spaced from the metal plates 6 and then turn through 90° at 25 to enter a conventional thermocouple contact assembly 26. The contact assembly 26 is push fitted on a boss 27 integral with the second portion 4 of the sampling device. The contact assembly 26 is also slotted into a bore 28 of a paperboard tube 29 push fitted into the paperboard tube 1.

In use, a conventional lance including electrical circuitry for connection with the contact assembly 26 is inserted into the paperboard tube 29 until it mates with contacts 30 of the assembly 26.

The important advantages of this arrangement incorporating the temperature sensing device are that a single spot weld is required at 23, no complex insulation arrangements are needed to prevent heat from the second portion 4 affecting the copper wires 24, and that the sampling unit 2 provides a solid and firm body to which lighter peripheral components can be fitted. Previous designs required the use of front and back bungs supported by a paperboard tube.

I claim:

1. A metal melt sampling device comprising a sampling unit of refractory material for mounting in a support tube, said sampling unit including first and second portions and further means, said second portion being integral with said first portion and defining with said further means walls of a main sample cavity, said first portion defining a leading end of the unit; and an inlet passage to enable metal melt to pass in use from said leading end of said unit to said main sample cavity, wherein at least one of said first and second portions is adapted to be a push fit in said support tube and wherein said sampling unit defines an exposed surface adapted to initially contact metal melt, a portion of said inlet passage and said exposed surface being coated with refractory cement.

2. A device according to claim 1, wherein said further means comprises at least one metal plate connected to said second portion of said unit to close said main sample cavity.

3. A device according to claim 2, wherein said second portion of said sampling unit defines a pair of opposed openings over which a pair of said metal plates are secured.

4. A device according to claim 2 wherein said at least one plate is secured to said second portion of said sampling unit by a clip having at least one outwardly extending portion whereby on insertion of said sampling unit into said support tube said at least one outwardly extending portion of said clip is forced radially inwardly to assist securement of said at least one plate on said second portion of said sampling unit.

5. A device according to claim 1, further comprising at least one additional sample cavity defined by said second portion of said sampling unit and said further means, said at least one additional sample cavity communicating with said main sample cavity.

6. A device according to claim 5, wherein said at least one additional sample cavity is provided adjacent said inlet passage.

7. A metal melt sampling device comprising a sampling unit of refractory material for mounting in a support tube, said sampling unit including first and second portions and further means, said second portion being integral with said first portion and defining with said further means walls of main sample cavity, said first portion defining a leading end of the unit; and an inlet passage to enable metal melt to pass in use from said leading end of said unit to said main sample cavity, wherein at least one of said first and second portions is adapted to be a push fit in said support tube and, wherein a portion of said walls of said main sample cavity is shaped to produce, in use, a locating formation in the sample of metal melt, whereby a solidified sample extracted from said main sample cavity may be located by said locating formation during preparation of a surface of said sample for analysis.

8. A device according to claim 7, wherein said portion of said walls of said main sample cavity which is shaped to produce said locating formation is that portion opposite to a portion of the walls which moulds the surface of the sample for analysis.

9. A device according to claim 7 or claim 8, wherein said portion of said walls of said main sample cavity shaped to produce the locating formation is a recess whereby after solidification, the metal sample has a protruding boss integrally formed on it to provide the locating formation.

10. A device according to claim 1, wherein said sampling unit is made of bonded sand.

11. A device according to claim 1, further including a support tube into which said sampling unit is push fitted, said support tube defining a leading end.

12. A metal melt sampling device comprising a sampling unit of refractory material for mounting in a support tube, said sampling unit including first and second portions and further means, said second portion being integral with said first portion and defining with said further means walls of a main sample cavity, said first portion defining a leading end of the unit; and an inlet passage to enable metal melt to pass in use from said leading end of said unit to said main sample cavity, wherein at least one of said first and second portions is adapted to be a push fit in said support tube, said device further including a support tube into which said sampling unit is push fitted, said support tube defining a leading end, wherein said support tube is made of a paperboard, the device further comprising paperboard cover over said leading end of said support tube adapted to protect said sampling unit on insertion into a metal melt.

13. A stream sampler according to claim 11, said first portion of said sampling unit protruding from and abutting said leading end of said support tube, said first portion tapering towards said leading end of said unit, said second portion of the sampling unit being push fitted into said support tube, and the sampler further including a silica inlet tube mounted in and protruding from said inlet passage.

14. A device according to claim 1, further comprising a temperature sensing device secured to said sampling unit.

15. A method of manufacturing a sampling device according to claim 1, the method comprising providing moulding apparatus having means for defining said main sample cavity; supplying bondable sand to said moulding apparatus; heating said moulding apparatus and allowing the sand to solidify to define a sampling unit; extracting said solidified unit; securing at least one metal plate on said unit to close said sample cavity; providing an inlet passage; and mounting said sampling unit in a support tube.

16. A method of manufacturing a sampling device comprising a sampling unit of refractory material for mounting in a support tube, said sampling unit including first and second portions and further means, said second portion being integral with said first portion and defining with said further means walls of a main sample cavity, said first portion defining a leading end of the unit; and an inlet passage to enable metal melt to pass in use from said leading end of said unit to said main sample cavity, wherein at least one of said first and second portions is adapted to be a push fit in said support tube, the method comprising providing moulding apparatus having means for defining said main sample cavity; molding green ceramic with said moulding apparatus; heating said moulded ceramic to form a sampling unit; securing at least one metal plate on said unit to close said sample cavity; providing an inlet passage; and mounting said sampling unit in a support tube.

17. A method according to claim 15 or claim 16, wherein said moulding apparatus has means for defining said inlet passage.

18. A metal melt sampling device comprising a sampling unit of refractory material for mounting in a support tube, said sampling unit including first and second portions and at least one metal plate, said second portion being integral with said first portion and defining with said at least one metal plate walls of a main sample cavity, said first portion defining a leading end of a unit, wherein said at least one metal plate is secured to said second portion of said sampling unit by a generally U-shaped clip, portions of said clip adjacent a bight of said U converging and arms of said clip subsequently diverging to an extent sufficient that, in use, when said clip is mounted on said second portion of said sampling unit, said diverging portions of said clip are adapted to engage said support tube whereby on insertion of said sampling unit into said support tube said arms of said clip are forced radially inwardly to assist securement of said at least one metal plate on said second portion of said sampling unit; and an inlet passage to enable metal melt to pass in use from said leading end of said unit to said main sample cavity, wherein at least one of said first and second portions is adapted to be a push-fit in said support tube.

* * * * *